US010172895B2

(12) United States Patent
Kim et al.

(10) Patent No.: US 10,172,895 B2
(45) Date of Patent: Jan. 8, 2019

(54) **PHARMACEUTICAL COMPOSITION CONTAINING *SCEPTRIDIUM JAPONICUM* EXTRACT FOR PREVENTING OR TREATING STROKE OR DEGENERATIVE BRAIN DISEASES**

(71) Applicant: UNIVERSITY-INDUSTRY COOPERATION GROUP OF KYUNG HEE UNIVERSITY, Gyeonggi-do (KR)

(72) Inventors: Hocheol Kim, Seoul (KR); Donghun Lee, Seoul (KR); Jungbin Song, Seoul (KR); Jin Gyu Choi, Seoul (KR); Sung Hyun Lee, Gyeonggi-do (KR)

(73) Assignee: University-Industry Cooperation Group of Kyung Hee University, Gyeonggi-do (KR)

( * ) Notice: Subject to any disclaimer, the term of this patent is extended or adjusted under 35 U.S.C. 154(b) by 657 days.

(21) Appl. No.: 14/648,240

(22) PCT Filed: Nov. 28, 2013

(86) PCT No.: PCT/KR2013/010879
§ 371 (c)(1),
(2) Date: Sep. 11, 2015

(87) PCT Pub. No.: WO2014/084616
PCT Pub. Date: Jun. 5, 2014

(65) Prior Publication Data
US 2016/0008414 A1 Jan. 14, 2016

(30) Foreign Application Priority Data
Nov. 28, 2012 (KR) .................. 10-2012-0135928

(51) Int. Cl.
*A61K 36/00* (2006.01)
*A61K 36/11* (2006.01)
*A23L 33/105* (2016.01)

(52) U.S. Cl.
CPC ............ *A61K 36/11* (2013.01); *A23L 33/105* (2016.08)

(58) Field of Classification Search
None
See application file for complete search history.

(56) References Cited

U.S. PATENT DOCUMENTS

| 5,601,829 A | 2/1997 | Eliseo Almagro et al. 424/195.1 |
| 2004/0253647 A1* | 12/2004 | Mathews ........... G01N 33/5008 435/7.2 |

FOREIGN PATENT DOCUMENTS

| CN | 1241415 A | 1/2000 |
| CN | 102294004 | 12/2011 |
| CN | 102294004 A | * 12/2011 |
| CN | 102294004 A | * 12/2011 |
| CN | 102670979 | 9/2012 |
| JP | H07-304681 | 11/1995 |
| JP | 2005-089375 A | 4/2005 |
| KR | 10-2007-0041489 | 4/2007 |
| KR | 10-2011-0134612 | 12/2011 |
| WO | WO 2002/047707 | 6/2002 |

OTHER PUBLICATIONS

Vickers (A Vaccine Against Alzheimer's Disease, Drug Aging. 2002. vol. 19, No. 2, pp. 487-494.*
U.S. Appl. No. 14/361,243, filed Oct. 13, 2014, 2015/0065441, Mar. 5, 2015.
U.S. Appl. No. 14/785,312, filed Oct. 16, 2015.
Letter/Written Disclosure of the Supplemental Information Disclosure Statement for the above-referenced application, filed herewith on Dec. 1, 2017, 2 pages.
Response, filed Feb. 20, 2017, to Extended European Search Report, dated Jul. 25, 2016, in connection with European Patent Application No. 13858783.7, 10 pages.
Communication Pursuant to Article 94(3) EPC (Examination Report), dated May 18, 2017, in connection with European Patent Application No. 13858783.7 [D1 =Database WPI Week 201280, Thomson Scientific, London, GB; AN 2012-A90264, XP002759795, & CN 102 294 004 A; D2 = Database TCM SIPO; Oct. 19, 2000, Wang Liang, entitled "A medicine for the treatment of rheumatism, and its preparation method," XP002759796, CN-98112553-A & CN 1 241 415 A; D3 = WO 2002/047707 A2], 4 pages.
Response, filed Jul. 18, 2017, to Communication Pursuant to Article 94(3) EPC (Examination Report), dated May 18, 2017, in connection with European Patent Application No. 13858783.7, 43 pages.
Communication Pursuant to Article 94(3) EPC (Examination Report), dated Aug. 3, 2017, in connection with European Patent Application No. 13858783.7 [D1 =Database WPI Week 201280, Thomson Scientific, London, GB; AN 2012-A90264, XP002759795, & CN 102 294 004 A; D3 = WO 2002/047707 A2], 4 pages.
Letter/Written Disclosure of the Supplemental Information Disclosure Statement for the above-referenced application, filed herewith on Aug. 10, 2016, 2 pages.
Database TCM entitled "A medicine for the treatment of rheumatism, and its preparation method," [published on Jan. 19, 2000] [online] AN: CN-98112553-A, XP002759796, 1 page.
Database WPI Week 201280 [published on Dec. 28, 2011] [online] Thomson Scientific, London. GB; AN: 2012-A90264, XP002759795, 4 pages.

(Continued)

*Primary Examiner* — Christopher R Tate
*Assistant Examiner* — Randall Winston
(74) *Attorney, Agent, or Firm* — Rubin and Rudman LLP (57) ABSTRACT

The present invention provides a pharmaceutical composition containing a *Sceptridium japonicum* extract, as an active ingredient, for preventing or treating stroke or degenerative brain diseases. The *Sceptridium japonicum* extract of the present invention has a protective effect on cranial nerves so as to exhibit a functional effect of preventing or treating stroke or various degenerative brain diseases.

4 Claims, 7 Drawing Sheets

(56) References Cited

OTHER PUBLICATIONS

Database WPI Week 201311 [published on Jun. 8, 2012] Thomson Scientific, London, GB; AN: 2012-Q45178, XP002759798, 3 pages.
Rana et al., "Diversity, indigenous uses and conservation status of medicinal plants in Manali wildlife sanctuary, North western Himalaya," Indian Journal of Traditional Knowledge 10(3):439-459 (2011).
Extended European Search Report, dated Jul. 25, 2016, in connection with European Patent Application No. 13858783.7, 10 pages.
Letter/Written Disclosure of the Information Disclosure Statement for the above-referenced applications, dated Nov. 25, 2015, 2 pages.
Calderon-Montano et al., "A review on the dietary flavonoid Kaempferol," Mini Rev Med Chem. 11(4):298-344 (2011).
Crain et al., "Selective neuronal death after transient forebrain ischemia in the Mongolian gerbil: a silver impregnation study." Neuroscience, 27(2):387-402 (1988).
Flowers, F. and J. Zimmerman, "Reactive oxygen species in the cellular pathophysiology of shock," New Horiz. 6:169-180 (1998) [abstract only; available at http://www.ncbi.nlm.nih.gov/pubmed/?term=Flowers+F%2C+Zimmerman+JJ.+New+Horiz.+6%3A169-180%2C+1998].
Kang et al., "Chronological changes of N-methyl-D-aspartate receptors and excitatory amino acid carrier 1 immunoreactivities in CA1 area and subiculum after transient forebrain ischemia." J. Neurocytol. 30:945-955 (2001).
Kim et al., "Protective Effects of Kaempferol (3,4',5,7-tetrahydroxyflavone) against Amyloid Beta Peptide (Aβ)-Induced Neurotoxicty in ICR Mice," Biosci Biotechnol Biochem. 74(2):397-401 (2010).
Kirino T. and Sano, K.,"Selective vulnerability in the gerbil hippocampus following transient ischemia," Acta Neuropathol.62(3): 201-208 (1984).
Kirino T., "Delayed neuronal death in the gerbil hippocampus following ischemia," Brain Res., 239:57-69 (1982).
Lee et al., "Photochemically induced cerebral ischemia in a mouse model." Surgical Neurology, 67(6): 620-625 (2007).
Longa et al., "Reversible middle cerebral artery occlusion without craniectomy in rats." Stroke 20(1):84-91 (1989).
Machine English translation of Japanese Patent Publication No. JP 2005-089375 A (App. No. JP 2003-0325711), Japan Platform for Patent Information, 15 pages.
Machine English translation of Korean Patent Publication No. KR 10-2007-0041489 (App. No. KR 10-2007-0031959), Korean Intellectual Property Office, 15 pages.
Machine English translation of Korean Patent Publication No. KR 10-2011-0134612 (App No. KR 10-2010-0054270), Korean Intellectual Property Office, 32 pages.
Pulsinelli, W. and J. Brierley, "A new model of bilateral hemispheric ischemia in the unanesthetized rat," Stroke, 10(3):267-272 (1979).
Sun, A, and Y. Chen, "Oxidative stress and neurodegenerative disorders," J. Biomed. Sci., 5:401-414 (1998).
Tanaka et al., "Chemical and Chemotaxonomic Studies of Pterophytens. LXIV. Chemical Studies on the Constituents of Sceptridium ternatum var ternatum" Chem Pharm Bull (Tokyo) 34(9):3727-3732 (1986) [Article in German with English language abstract].
Won et al., "Immunohistochemical detection of oxidative DNA damage induced by ischemia-reperfusion insults in gerbil hippocampus in vivo." Brain Res. 836:70-78 (1999).
International Search Report and Written Opinion, dated Apr. 1, 2014, in connection with International Patent Application No. PCT/KR2013/010879 [English translation], 11 pages.
International Preliminary Report on Patentability, dated Jun. 2, 2015, International Patent Application No. PCT/KR2013/010879 [English translation], 8 pages.

\* cited by examiner

Fig 1.

Control     *S. ternatum*
100 mg/kg, i.p.

Control    *S. ternatum*
600 mg/kg, p.o.

Control    120    400    1200
           *S. ternatum*
           mg/kg, p.o.

PHARMACEUTICAL COMPOSITION CONTAINING *SCEPTRIDIUM JAPONICUM* EXTRACT FOR PREVENTING OR TREATING STROKE OR DEGENERATIVE BRAIN DISEASES

RELATED APPLICATIONS

This application is the U.S. National Stage of International Application No. PCT/KR2013/010879, filed 28 Nov. 2013, which claims benefit of priority to Korean Patent Application KR 10-2012-0135928, filed 28 Nov. 2012, the specification of each of which is incorporated by reference herein.

TECHNICAL FIELD

The present invention relates to a pharmaceutical composition comprising a *Sceptridium ternatum* extract for preventing or treating strokes or degenerative brain diseases.

BACKGROUND ART

According to a report issued October 2003 by Statistics Korea, 7.2% of the total population of South Korea was 65 or older in 2000, indicating the entry of the country into the category of an aging society. By 2019, Korean society is expected to become an aged society as the elderly population will reach 14% or higher. With the rise of aging problems as a social issue, nationwide attention has intensively been paid to elderly welfare such as characteristics, living, health, culture, and leisure of the elderly population, together with an increasing demand for statistical data on welfare. One of the most important problems occurring with an increase in the elderly population is chronic degenerative diseases. This is in contrast to acute infectious diseases, which have been the main cause of death over the past five decades. Of chronic degenerative diseases, cerebrovascular diseases are observed to rank second among all mortality attributed to individual diseases.

Cerebrovascular diseases are largely divided into two types: hemorrhagic cerebral diseases, such as cerebral hemorrhage, and ischemic cerebral diseases, such as that caused by cerebrovascular occlusion. While traffic accidents account for many cases of hemorrhagic cerebral diseases, ischemic cerebral diseases is frequently observed in the elderly.

Transient cerebral ischemia, if introduced, blocks the supply of oxygen and glucose to the cerebrum, with the subsequent decrease of ATP levels and the generation of edema in neural cells, resulting in damage over a wide region of the brain. Death of neural cells is observed when a significant period of time is passed after the occurrence of cerebral ischemia, and thus is called delayed neuronal death. An experiment conducted on a transient forebrain ischemic model using Mongolian gerbils reported that neuronal death occurs in the CA1 region of the hippocampus four days after the introduction of cerebral ischemia for 5 min (Kirino T, Sano K. *Acta Neuropathol.*, 62: 201-208, 1984; Kirino T. *Brain Res.*, 239: 57-69, 1982).

Thus far, two mechanisms of cerebral ischemia-induced neuronal death are known: one is the excitotoxic neuronal death mechanism, in which excessive glutamate accumulates outside cells upon cerebral ischemia, and flows into cells, with the concomitant intracellular accumulation of calcium, thereby inducing neuronal death (Kang T C, et al., *J. Neurocytol.*, 30: 945-955, 2001); and the other is oxidative neuronal death, in which abrupt oxygen supply upon ischemia-reperfusion increases free radical levels to give rise to the injury of the DNA and cytoplasm (Won M H, et al, *Brain Res.*, 836: 70-78, 1999; Sun A Y., Chen Y M., *J. Biomed. Sci.*, 5: 401-414, 1998; Flowers F, Zimmerman J J, *New Horiz*, 6: 169-180, 1998).

On the basis of the disclosed mechanisms of ischemia-induced neuronal death, much research has been directed toward materials that can inhibit ischemia-induced neuronal death, together with their functional mechanisms. However, almost no materials that inhibit cerebral ischemia-induced neutral death effectively have yet been found.

Tissue plasminogen activator, which is a commercially available cerebral ischemia treating agent solely approved by the FDA, is thrombolytic agent that break down the blood clots to induce for the rapid supply of oxygen and glucose to the brain. However, tissue plasminogen activator must be used immediately, as it does not directly protect nerve cells. Moreover, the thrombolytic function has the risk of causing hemorrhagic cerebral diseases when the agent is used frequently or in excessive doses.

MK-801, a calcium channel blocker for effectively inhibiting early-stage calcium ion influx, was abandoned as it was found to have adverse effects during clinical trials thereof.

Meanwhile, in South Korea, many health care foods containing natural substances are on the market and are promoted as being preventive of stroke. However, most such products have not yet been scientifically verified, and are frequently abused, causing various social problems.

There is therefore an urgent need for the development of a natural substance that is scientifically proven for therapeutic or preventive effects on cerebral diseases.

*Sceptridium ternatum* is a perennial grass taxonomically classified in the Ophioglossaceae family of the Ophioglossoides order in Pteridophyta. In South Korea, the plant grows naturally in high mountains in Jeju Island, Jiri Mountain, Deogyu Mountain, Kyeongnam province, Kyeongbuk province, Kangwon province, and Kyeonggi province, and is frequently found in semi-shaded grasslands in fertile soil and humid environments.

Nowhere has research into the neuroprotective effect of *Sceptridium ternatum* extracts on brain nerve cells, particularly in animal models, been reported.

DISCLOSURE

Technical Problem

It is an object of the present invention to provide a pharmaceutical composition for preventing or treating strokes or degenerative brain diseases, comprising a *Sceptridium ternatum* extract as an active ingredient.

It is another object of the present invention to provide a health functional food for preventing or ameliorating strokes or degenerative brain diseases, comprising a *Sceptridium ternatum* extract as an active ingredient.

It is a further object of the present invention to provide a method for preventing or treating strokes or degenerative brain diseases, comprising administering to a subject in need thereof a composition comprising a *Sceptridium ternatum* extract as an active ingredient.

Technical Solution

In accordance with an aspect thereof, the present invention provides a pharmaceutical composition for treating or preventing strokes or degenerative brain diseases, comprising a *Sceptridium ternatum* extract as an active ingredient.

In one embodiment of the present invention, the degenerative brain diseases may be selected from the group consisting of dementia, Alzheimer's disease, Parkinson's disease, Huntington's disease, Pick's disease, Creutzfeldt-Jakob disease, and a combination thereof.

In another embodiment of the present invention, the *Sceptridium ternatum* extract may be preferably obtained from a whole *Sceptridium ternatum* plant.

In another embodiment of the present invention, the extract may be obtained by extraction with a solvent selected from the group consisting of water, an alcohol, and a mixture thereof, the alcohol being preferably a C1~C4 lower alcohol, and most preferably ethanol.

In accordance with another aspect thereof, the present invention provides a health functional food for preventing or ameliorating strokes or degenerative brain diseases, comprising a *Sceptridium ternatum* extract as an active ingredient.

In accordance with a further aspect thereof, the present invention provides a method for preventing or treating strokes or degenerative brain diseases, comprising administering to a subject in need thereof a composition comprising a *Sceptridium ternatum* extract as an active ingredient.

Advantageous Effects

Having effective neuroprotective activity on brain nerve cells, the *Sceptridium ternatum* extract of the present invention finds application in preventing, treating, or ameliorating strokes or degenerative brain diseases.

BEST MODE

Below, a detailed description will be given of the present invention.

An aspect of the present invention addresses a pharmaceutical composition for preventing or treating strokes or degenerative brain diseases, comprising a *Sceptridium ternatum* extract as an active ingredient.

Preparation Method of *Sceptridium ternatum* Extract

The *Sceptridium ternatum* extract may be preferably prepared by a method including, but not limited to, the steps of:

(1) drying and pulverizing *Sceptridium ternatum*;

(2) extracting the pulverized *Sceptridium ternatum* with a extraction solvent;

(3) cooling and filtering the extract; and (4) concentrating the filtrate in a reduced pressure, followed by drying the concentrate.

Without limitations thereof, any *Sceptridium ternatum*, whether cultured directly or purchased, may be used in step (1). Preferred is a Whole *Sceptridium ternatum* Plant.

The extracting of step (2) may be conducted using, without limitation, a shaking extraction method, a Soxhlet extraction method, or a reflux extraction method. For the extraction, preferably a temperature of 40 to 100° C., and more preferably 60 to 80° C. may be set. In addition, the extraction may be preferably carried out for 2 to 24 hrs, and may be preferably repeated one to five times.

As the extraction solvent of step (2), water, an alcohol or a mixture thereof may be used. The alcohol may be preferably a lower alcohol of C1~C4, and most preferably methanol or ethanol. In addition, the extraction solvent is used in a weight or volume of preferably 5 to 15 times, and more preferably 10 times as much as the dried *Sceptridium ternatum* of step (1).

The reduced pressure concentration of step (4) may be preferably accomplished using a vacuum reduced pressure concentrator or a rotary vacuum evaporator, while the concentrate may be preferably dried using, without being limited thereto, a vacuum drying method, a reduced-pressure drying method, a boiling drying method, a spray drying method, or a freeze drying method.

Pharmaceutical Composition

The *Sceptridium ternatum* extract obtained by the above method was found to have excellent neuroprotective effects on cerebral ischemia-induced neuronal injury, as evaluated in middle cerebral artery occlusion (MCAo) models, photochemical thrombosis mouse models (PTB), and 4-vessel occlusion models (4-VO).

Accordingly, contemplated in accordance with another aspect of the present invention is a pharmaceutical composition for preventing or treating neural death-induced strokes or degenerative brain diseases, comprising the neuroprotective *Sceptridium ternatum* extract as an active ingredient.

The degenerative brain disease may be selected from the group consisting of dementia, Alzheimer's disease, Parkinson's disease, Huntington's disease, Pick's disease and Creutzfeldt-Jakob disease.

Preferably, the pharmaceutical composition may contain the *Sceptridium ternatum* extract of the present invention in an amount of 0.1 to 50 wt %, based on the total weight of the composition, but is not limited thereto.

In addition, the pharmaceutical composition of the present invention may be prepared into various dosage forms for oral and parenteral administration for use in clinical use. In this context, the pharmaceutical composition of the present invention may be formulated in combination with a diluent or excipient such as a filler, a extender, a binder, a humectant, a disintegrant, and a surfactant, etc.

Solid preparations intended for oral administration may be in the form of tablets, pills, powders, granules, capsules, and the like. In regards to these solid agents, the pharmaceutical composition of the present invention is formulated in combination with at least one excipient, e.g. starch, calcium carbonate, sucrose, lactose, and gelatin, etc. In addition to a simple excipient, a lubricant, such as magnesium stearate, or talc, may be used.

Among liquid preparations intended for oral administration are suspensions, internal use solutions, emulsion, syrups, and the like. Plus a simple diluent, such as water or liquid paraffin, various excipients, such as humectants, sweeteners, aromatics, preservatives, and the like, may be contained in the liquid preparations.

Also, the pharmaceutical composition of the present invention may be in a parenteral dosage form such as sterile aqueous solutions, non-aqueous solvents, suspensions, emulsions, lyophilizates, suppositories, and the like. Propylene glycol, polyethylene glycol, vegetable oils such as olive oil, and injectable esters such as ethyl oleate may be suitable for the non-aqueous solvents and suspensions. The basic materials of suppositories include Witepsol, Macrogol, Tween 61, cacao butter, laurin butter, glycerol, gelatin and the like. The pharmaceutical composition of the present invention may be parenterally administered by subcutaneous, intravenous, or intramuscular injection.

Depending on various factors including the patient's state and weight, the severity of disease, the form of drug, and the route and time of administration, the dose of the pharmaceutical composition in accordance with the present invention may vary and suitably selected by those skilled in the art. For a preferred effect, the extract of the present invention may be administered in a daily dose from 0.0001 to 100 mg/kg. The pharmaceutical composition according to the present invention may be administered in a single dosage, or may be divided into multiple dosages per day. However, the dosages are not intended to limit the range of the present invention.

For preventing or treating strokes or degenerative brain diseases, the composition of the present invention may be used alone or in combination with surgery, hormone therapy, chemical therapy or biological response modulators.

Health Functional Food

In accordance with a further aspect thereof, the present invention addresses a health functional food comprising a *Sceptridium ternatum* extract as an active ingredient for the preventing or ameliorating strokes or degenerative brain diseases.

In the health functional food of the present invention, the *Sceptridium ternatum* extract may be used individually, or in combination with other foods or food ingredients and may be used suitably according to the conventional methods. The content of the active ingredient in the health functional food may be determined according to the purpose of the composition (e.g., prevention, treatment or health aid). Generally, the active ingredient of the present invention may be added in an amount of 0.01 to 15 wt % based on the total weight of the food, when used to prepare foods or drinks.

Further, there is no particular limitation on the kind of health functional food of the present invention. Examples of such a health functional food include beverages, gums, multi-vitamins, drinks, etc., and cover all health functional foods in a typical context.

The health functional drink according to the present invention may further contain various fragrant or natural carbohydrates, etc as an additive. Examples of the natural carbohydrates include monosaccharides such as glucose and fructose, etc, disaccharide such as maltose and sucrose, etc, polysaccharides for example, conventional sugar such as dextrin and cyclodextrin, and sugar alcohols such as xylitol, sorbitol, erythritol, etc. Also, other fragrant, not described in the above (saccharin, aspartam, etc.), can be used.

In addition, the health functional food of the present invention may contain various nutrients, vitamins, minerals (electrolytes), flavors, whether synthetic or natural, colorants and enhancers (cheese, chocolate, etc.), pectic acid and salts thereof, alginic acid and salts thereof, organic acids, protective colloidal thickeners, pH modifiers, stabilizers, antiseptics, glycerin, alcohols, and carbonating agents used in carbonated beverages.

Method for Preventing or Treating of Strokes or Degenerative Brain Diseases

In accordance with a still further aspect thereof, the present invention addresses a method for preventing or treating strokes or degenerative brain diseases, comprising administering to a subject in need thereof a composition comprising *Sceptridium ternatum* as an active ingredient.

The pharmaceutical composition of the present invention falls within the scope of the composition used in the preventing or treating method of the present invention.

In addition, the *Sceptridium ternatum* extract contained in the composition may be obtained according to the extraction method of the present invention, and the extract may be preferably obtained from a whole *Sceptridium ternatum* plant.

In another embodiment of the present invention, the *Sceptridium ternatum* extract may be obtained by extraction with a solvent selected from the group consisting of water, an alcohol, and a mixture thereof. The alcohol is preferably a C1~C4 lower alcohol, and most preferably methanol or ethanol.

Further, the subject to which the preventing or treating method of the present invention is applied includes mammals, especially humans.

In another embodiment of the present invention, the degenerative brain disease may be selected from the group consisting of dementia, Alzheimer's disease, Parkinson's disease, Huntington's disease, Pick's disease, and Creutzfeldt-Jakob disease.

According to the preventing or treating method of the present invention, strokes and degenerative brain diseases can be effectively prevented or treated by administering a composition comprising the *Sceptridium ternatum* extract to mammals including humans.

MODE FOR INVENTION

A better understanding of the present invention may be obtained through the following examples which are set forth to illustrate, but are not to be construed as limiting the present invention.

PREPARATION EXAMPLE

Preparation of *Sceptridium ternatum* Extract

300 Grams of whole plants of *S. ternatum*, purchased from a Bozhou market in Anhui Province, China, were finely cut, and immersed in 3 L of a 70% aqueous ethanol solution. After one round of reflux extraction at 80° C. for 3 hrs, the extract was filtered through a filter paper. This filtrate was concentrated with reduced pressure, and lyophilized to afford a *Sceptridium ternatum* extract. 24.08 g (yield: 8.03%).

Example 1

Assay for Neuroprotective Effect of *Sceptridium ternatum* Extract—Middle Cerebral Artery Occlusion (MCAo) Model <1-1>Preparation of Experimental Animal Male Sprague-Dawley rats (Samtako Inc., Korea), 8 weeks old, each weighing about 300 g, were purchased for use as experimental animals. They were acclimated to the experimental environment while being allowed to freely access water and feed for one week before starting the experiment.

<1-2>Assay for Neuroprotective Effect

The neuroprotective activity of the *Sceptridium ternatum* extract against focal cerebral ischemia-induced neuronal injury was evaluated using an intraluminal suture method (*Zea Longa* et al., *Stroke*, 20:84-91, 1989).

Briefly, a 4-0 nylon suture was cut into a 22 mm-long segment. A 5-8 mm-long tip of the segmented suture was coated with silicon until the diameter reached 0.36 mm. Each rat was generally anesthetized with 5% isoflurane gas in a mixture of 70% $N_2O$ and 30% $O_2$, and then inserted with a syringe in on side to withdraw blood therefrom, and with a blood pressure probe in the other side to monitor blood pressures. The blood sample taken was analyzed for blood sugar and gas levels.

First, the incision was made on a fore-central area of the neck to carefully isolate the right carotid artery and the external carotid artery (ECA) from surrounding tissues and nerves. Thereafter, the superior parathyroid artery and the occipital artery, which are both branches of ECA, were electrically cauterized. The pterygoid palatine artery, which is a branch of the internal carotid artery, was treated with electrocautery, and the ECA was cut. The probe was inserted from the ECA to the internal carotid artery to a distance spaced about 18~19 mm apart from the common carotid artery bifurcation, and then fixed with a thread. The skin incision was sutured, and the rats were allowed to naturally awaken from anesthesia. The same number of rats from each of the groups was operated on while the body temperature was maintained at 37±0.5° C. Ninety minutes after the operation, the rats were re-anesthetized in the same manner as mentioned above, and the probe was withdrawn to reperfuse.

Twenty four hours after reperfusion, the rats were sacrificed by cervical dislocation, and the brain was excised within 2 min after cervical dislocation, and sectioned into 6 pieces, each 2 mm thick. These brain tissue sections were completely immersed in a 2% TTC (triphenyltetrazolium chloride) solution in 12-well plates, and incubated at 37° C. for 30 min. For observation, the tissues were fixed with 4% paraformaldehyde. All operation procedures were performed under an operating microscope. Anesthesia was maintained with 2% isoflurane during operation while a lamp was used to prevent the body temperature from decreasing below 37° C. Images of the stained brain tissues were taken using a digital camera, and stored in a computer. Cerebral infarct rates (%) were calculated using the image analysis program Optimas 6.5 (Bioscan) according to the following Mathematical Formula 1. In this regard, a normalized cerebral infarct volume ($mm^3$) was calculated according to the following Mathematical Formula 2.

$$\text{Cerebral Infarct Rate (\%)} = \frac{A - B}{A} \times 100 \quad \text{[Math Formula 1]}$$

A: normal left-hemisphere volume ($mm^3$)
B: normalized cerebral infarct volume ($mm^3$)

Normalized cerebral infarct volume($mm^3$)=(Volume of normal left hemisphere)−(Volume of normal area of injured hemisphere) [Math Formula 2]

<1-3>Administration of *Sceptridium ternatum* Extract

Intraperitoneal Administration

Immediately after the introduction of ischemia, the *S. ternatum* extract was intraperitoneally injected into the rats at a dose of 100 mg/kg. In this regard, a dilution of the extract in physiological saline containing 5% dimethylsulfoxide was injected in a volume of 1 ml per 100 g of rat weight. For a control, the same volume of 5% DMSO in physiological saline was used.

Oral Administration

Immediately after the introduction of ischemia, the *S. ternatum* extract was orally administered to the rats at a dose of 600 mg/kg. In this regard, a dilution of the extract in physiological saline containing 5% dimethylsulfoxide was administered in a volume of 1 ml per 100 g of rat weight. For a control, the same volume of 5% DMSO in physiological saline was used.

<1-4>Neuroprotective Effect of *Sceptridium ternatum*

Intraperitoneal Administration

Figure 1:
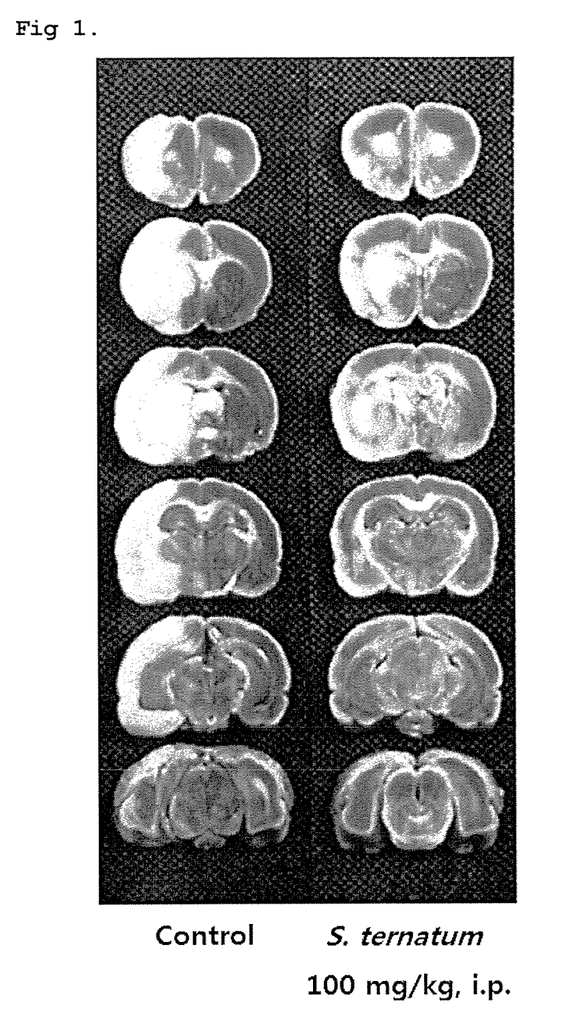
FIG. 1 shows images of TTC-stained brain sections of rats intraperitoneally injected with 5% DMSO as a control group, or with the *Sceptridium ternatum* extract of the present invention as a test group at a dose of 100 mg/kg in the middle cerebral artery occlusion (MCAo) models.

Examination was made of the protective effect of the *Sceptridium ternatum* extract on brain tissues and cerebral nerve cells. Compared to the control, the test groups administered with the *Sceptridium ternatum* extract were observed to have smaller areas that were not stained with TTC, and larger TTC-stained, dark red areas, indicating that the extract has a neuroprotective effect. When stained with TTC, brain tissue appears to be white in areas where nerve cells are dead, and dark red in normal areas (FIG. 1).

Figure 2:
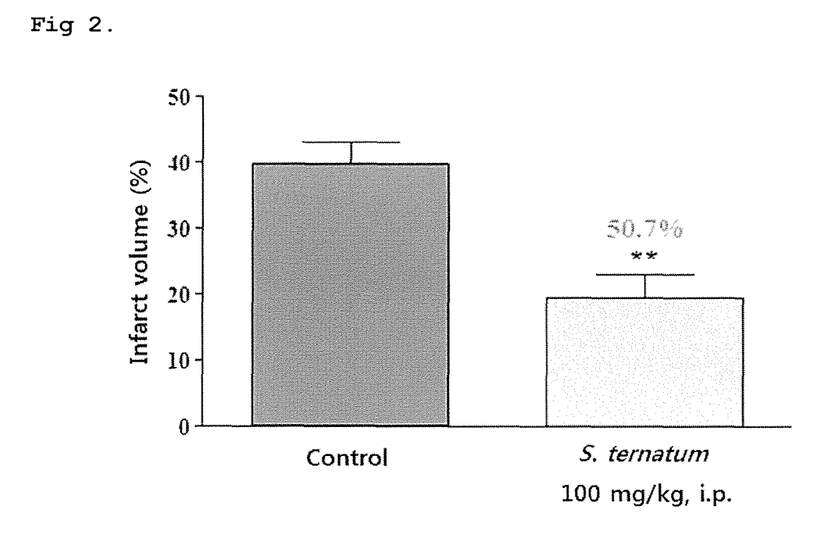
FIG. 2 is a graph of brain tissue injury ratios (brain infarct ratios) compared between the control or test groups intraperitoneally injected in the middle cerebral artery occlusion (MCAo) models intraperitoneally injected.

As can be seen from the data on the neuroprotective activity of the *Sceptridium ternatum* extract against middle cerebral artery occlusion-induced neuronal death, an infarct volume was measured to be 19.6±3.3% at 100 mg/kg (i.p), which was improved by 50.7%, compared to 39.7±3.3% for the control, indicating a significant neuroprotective effect of the extract upon i.p. administration (p<0.01) (FIG. 2).

Oral Administration

Figure 3:
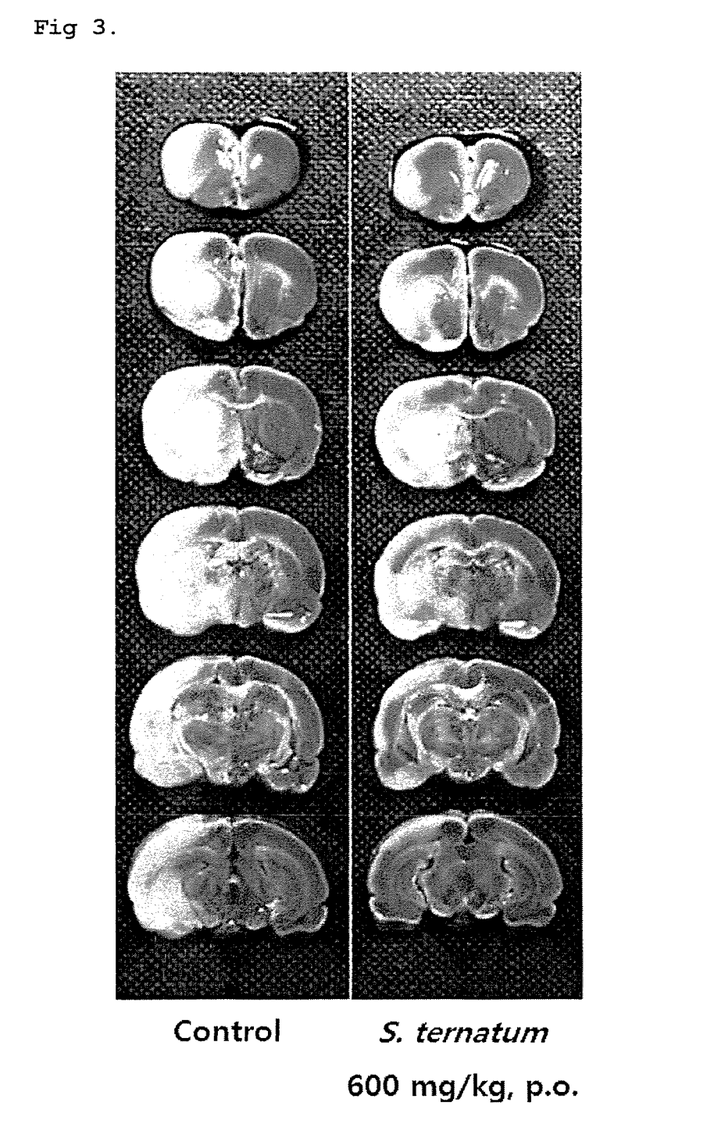
FIG. 3 shows images of TTC-stained brain sections of rats orally administered with 5% DMSO as a control or with the *Sceptridium ternatum* extract of the present invention as a test group at a dose of 600 mg/kg in the middle cerebral artery occlusion (MCAo) models.

Examination was made of the protective effect of the *Sceptridium ternatum* extract on brain tissues and cerebral nerve cells. Compared to the control, the test groups administered with the *Sceptridium ternatum* extract were observed to have smaller areas that were not stained with TTC, and larger TTC-stained, dark red areas, indicating that the extract has a neuroprotective effect. When stained with TTC, brain tissue appears to be white in areas where nerve cells are dead, and dark red in normal areas (FIG. 3).

Figure 4:
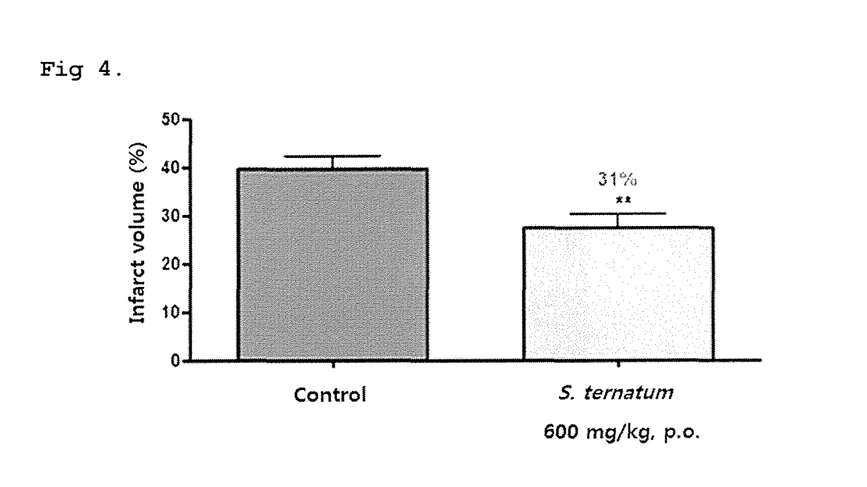
FIG. 4 is a graph of brain tissue injury ratios (brain infarct ratios) compared between control and test groups orally administered in the middle cerebral artery occlusion (MCAo) models.

As can be seen from the data on the neuroprotective activity of the *Sceptridium ternatum* extract against middle cerebral artery occlusion-induced neuronal death, an infarct volume was measured to be 27.4±2.7% at 600 mg/kg (p.o.), which was improved by 31%, compared to 39.6±2.6% for the control, indicating the significant neuroprotective effect of the extract upon p.o. administration (p<0.01) (FIG. 4).

Example 2

Assay for Neuroprotective Effect of *Sceptridium ternatum* Extract—Photochemical Thrombotic Mouse Model (PTB)

<2-1>Preparation of Experimental Animal

Male C57BL/6 mice (Samtako Inc., Korea), 8 weeks old, each weighing about 22 g, were purchased for use as experimental animals. They were acclimated to the experimental environment while being allowed to freely access water and feed for one week before starting the experiment.

<2-2>Assay for Neuroprotective Effect

The neuroprotective activity of the *Sceptridium ternatum* extract against focal cerebral ischemia-induced neuronal injury was evaluated using a photochemical thrombotic model with a modification (Lee, et al., *Surgical Neurology*, 67: 620-625, 2007).

After anesthesia by intraperitoneal injection of chloral hydrate at a dose of 450 mg/kg, the craniums of mice were placed in a head-holding adaptor (SG-4N, Narishige, Tokyo, Japan). A 1.5-cm scalp incision was made in an area that was intended to be a lesion, and the periosteum was removed to reveal the cranium. A fiber-optic light source (CL 6000 LED; Carl Zeiss, Gottingen, Germany) with a 4-mm aperture was centered at a marked point laterally 2 mm distant from the bregma. Five minutes after the intraperitoneal injection of 10 mg/ml Rose Bengal (Sigma-Aldrich, St. Louis, Mo.) at a dose of 0.1 ml to each mouse, the skull was irradiated for 15 min with the LED light source that did not generate heat while the aperture of the illuminator was placed close to the skull. Immediately after the introduction of ischemia, the *S. ternatum* extract prepared by the preparation example was orally administered at doses of 120, 400, and 1,200 mg/kg to the mice. In this regard, a dilution of the extract in physiological saline containing 5% dimethylsulfoxide was orally administered in a volume of 0.1 ml per 10 g of mouse weight. For a control, the same volume of 5% DMSO in physiological saline was used. Then, the incised skin was sutured, and the mice were allowed to naturally awaken from anesthesia. Twenty four hours after the introduction of ischemia, the mice were sacrificed, and the brain was excised within 2 min after sacrifice and sectioned into 5 pieces, each mm thick. These brain tissue sections were completely immersed in a 2% TTC (triphenyltetrazolium chloride) solution in plates, and incubated at 37° C. for 30 min. For observation, the tissues were fixed with 4% paraformaldehyde. Images of the stained brain tissues were taken using a digital camera and stored in a computer. Cerebral infarct volumes were measured using the image analysis program AxioVision Rel. 4.7. Cerebral infarct rates (%) were calculated according to the following Mathematical Formula 1. In this regard, a normalized cerebral infarct volume (mm$^3$) was calculated according to the following Mathematical Formula 2.

$$\text{Cerebral Infarct Rate (\%)} = \frac{A - B}{A} \times 100 \quad \text{[Math Formula 1]}$$

A: normal left-hemisphere volume (mm$^3$)
B: normalized cerebral infarct volume (mm$^3$)

Normalized cerebral infarct volume(mm$^3$)=(Volume of normal left hemisphere)−(Volume of normal area of injured hemisphere) [Math Formula 2]

Figure 5:
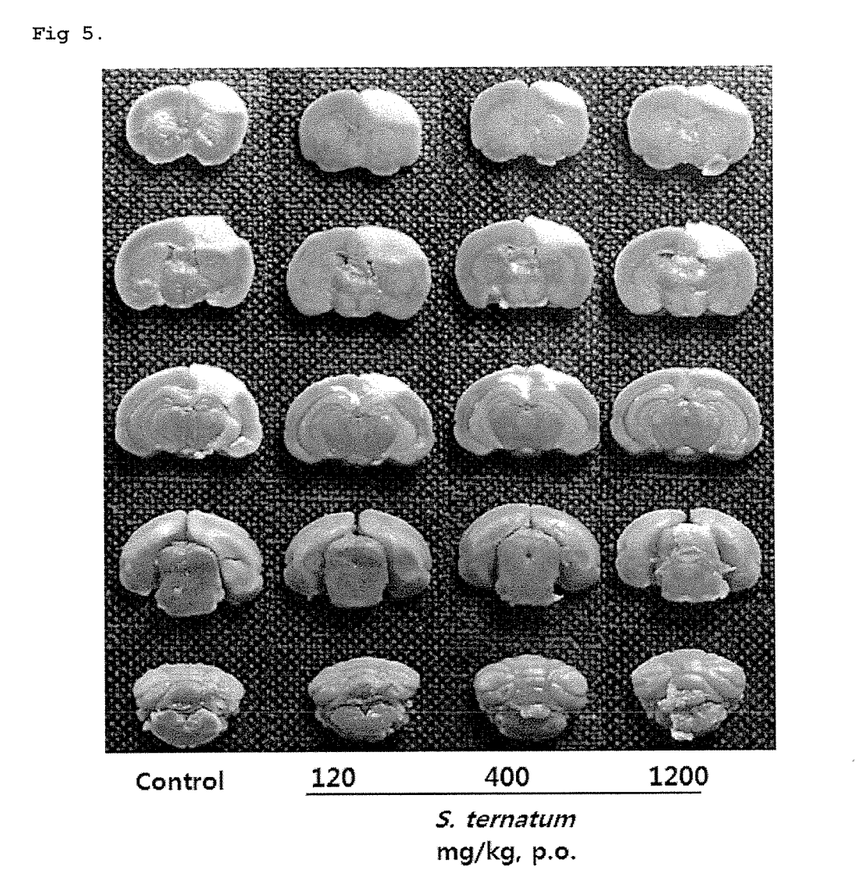
FIG. 5 shows images of TTC-stained brain sections of mice orally administered with 5% DMSO as a control or with the *Sceptridium ternatum* extract of the present invention as a test group at doses of 120, 400, and 1200 mg/kg in the photochemical thrombotic mouse models (PTB).

Examination was made of the protective effect of the *Sceptridium ternatum* extract on brain tissues and cerebral nerve cells. As can be seen in FIG. 5, the test groups administered with the *Sceptridium ternatum* extract were observed to have smaller areas that were not stained with TTC, and larger TTC-stained, dark red areas, compared to the control, which accounted for the neuroprotective effect of the extract (FIG. 5).

Figure 6:
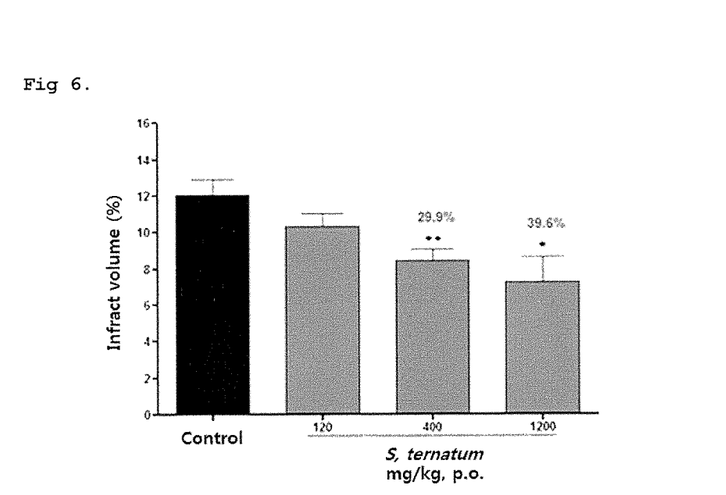
FIG. 6 is a graph of brain tissue injury ratios (brain infarct ratios) compared between control and test groups in the photochemical thrombotic mouse models (PTB).

The infarct volume was measured to be 10.3±0.69% at 120 mg/kg (p.o.), 8.45±0.57% at 400 mg/kg (p.o.), and 7.28±1.34% at 1200 mg/kg (p.o.). The infarct volumes of the latter two were respectively improved by 29.9 and 39.6%, compared to 12.05±0.83% for the control, indicating the significant neuroprotective effect of the extract upon p.o. administration at a dose of 400 or 1,200 mg/kg (FIG. 6).

Experimental Example 3

Assay for Neuroprotective Effect of *Sceptridium ternatum* Extract—4-Vessel Occlusion (4-VO) Model 3-1>Preparation of Experimental Animal Male Wistar rats (Samtako Inc., Korea), 7 weeks old, each weighing about 180 g, were purchased for use as experimental animals. They were acclimated to the experimental environment while being allowed to freely access water and feed for one week before starting the experiment.

<3-2>Assay for Neuroprotective Effect

The neuroprotective activity of the *Sceptridium ternatum* extract against cerebral ischemia-induced neuronal injury was evaluated using the 4-vessel occlusion model developed by Pulsinelli in 1979 (Pulsinelli W A, Brierley J B, Stroke, 10, 267-272, 1979).

After anesthesia with 5% isoflurane gas in a mixture of 70% nitrogen and 30% oxygen, each rat was secured in a sterotaxic apparatus so that its tail was downwardly oblique at an angle of 30° with regard to the horizon of the head. The nose and perioral area was covered with a plastic cone inhaler to maintain anesthesia during the operation by providing 1.5% isoflurane.

Experiments were conducted while the cervical spine was extended by tying on the rat's tail on a table. First, a neck midline incision was made from the occipital bone to expose the first cervical vertebra. Using a magnifying glass and taking caution to avoid causing injury to the muscles, a fine electrocautery probe with a diameter of 1 mm or less was inserted through the alar foramina of the first cervical vertebra into the tunnel through which the vertebral artery runs below the alar foramina. By intermittent electric supply, the vertebral artery was cauterized. After the permanent occlusion of the vertebral artery in the tunnel running through the bone was optically confirmed using a operating microscope, the incision was sealed with surgical clips.

Next, the pharynx was surgically operated. In this regard, a suture filament ring was applied to the common carotid artery in such a way as to induce ischemia and then to allow reperfusion. In order to block microvascular circulation upon ischemia, rear positions of the trachea, the esophagus, the external jugular vein, and the common carotid artery, and at front positions of the cervical and paravertebral muscles were penetrated by suture, and then the wound was sealed by surgical clips.

Then, the surgical clips were removed 24 hrs after the sealing. The common carotid artery was tied for 10 min with an aneurysm clip to induce ischemia. If the light reflex did not disappear within 1 min, the cervical sealing was further tightened. In this context, the rats in which the light reflex did not disappear were excluded, because the opposite parallel CA1 hippocampal neurons had not been completely injured. Convulsive rats were excluded, too. After 10 min of ischemia, the aneurysm clip was removed from the common carotid artery to cease the progression of ischemia and to allow reperfusion. Immediately and 90 min after reperfusion, the *Sceptridium ternatum* extract was intraperitoneally administered at a dose of 100 mg/kg.

One week after the introduction of ischemia, the rats were anesthetized by intraperitoneal injection of urethane at a dose of 1.2 g/kg, and the chest was opened to perform right atriotomy. A needle was inserted into the left ventricle, followed by perfusion with heparinized 5% sodium nitrate physiological saline for 10 min and then with 4.0% formalin fixative. Thereafter, the brain was excised, and fixed for 2 hrs with 0.1 M phosphate buffered formalin fixative before immersion in 30% sucrose solution overnight. The coronal block in the dorsal hippocampus, between −2.5 mm and −4.0 mm of the bregma, was excised from the fixed brain, and subjected to cryosection inducing hippocampus at −70° C. at 30 μm intervals using a sliding microtome.

The sections thus obtained were stained with cresyl violet and fixed. Subsequently, injured neurons were counted within a diameter of 1,000 μm in the middle zone, which is the most vulnerable to delayed neuronal death in the dorsal hippocampal CA1 sector (Crain B J et al., Neuroscience, 27, 387-402, 1988). For the enumeration, normal pyramidal cells were counted in a total of 6 sites, including two opposing left and right sites for each of three different sections of one brain tissue, by three observers with a high magnification (×400), and the mean values of the measurements were used.

The hippocampal tissue of the rats administered with 5% DMSO was used as a control while the *Sceptridium ternatum* extract was injected to the test groups.

For the control, neurons were observed to separate from surrounding cells, unlike normal neurons. It was observed that the cell body lost its native pyramidal morphology together with cell body shrinkage into single cell morphology. In addition, it was observed that nuclear chromatin was condensed, and membrane was collapsed, which indicated apoptosis.

Figure 7:
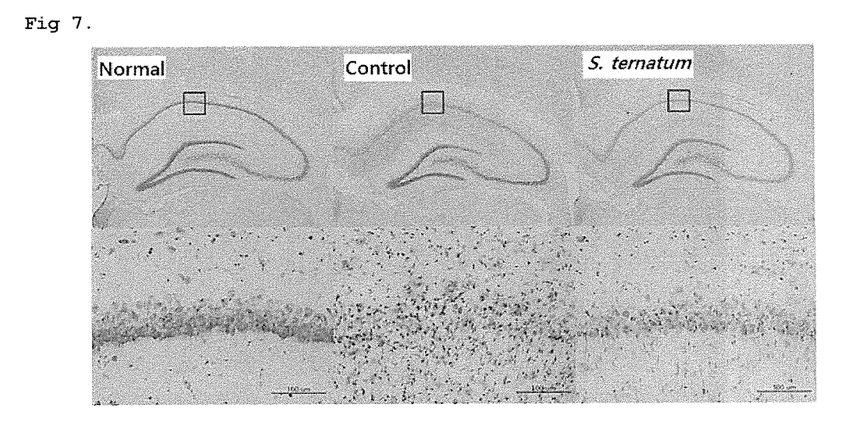
FIG. 7 shows images of hippocampal tissues of rats intraperitoneally injected with 5% DMSO for a control, or with the *Sceptridium ternatum* extract of the present invention as a test group at doses of 100, 400, and 1200 mg/kg in the 4-vessel occlusion (4-VO) models, explaining that neurons separate from surrounding cells.

The nerve cells from the group i.p. injected with the *Sceptridium ternatum* extract of the present invention at a dose of 100 mg/kg morphologically resembled normal cells, and were readily distinguished due to the stretching perikaryon and the central round nucleus. Being protected from apoptotic factors, most cells were found to retain normal pyramidal morphologies, and to maintain junction to adjacent cells (FIG. 7).

Figure 8:
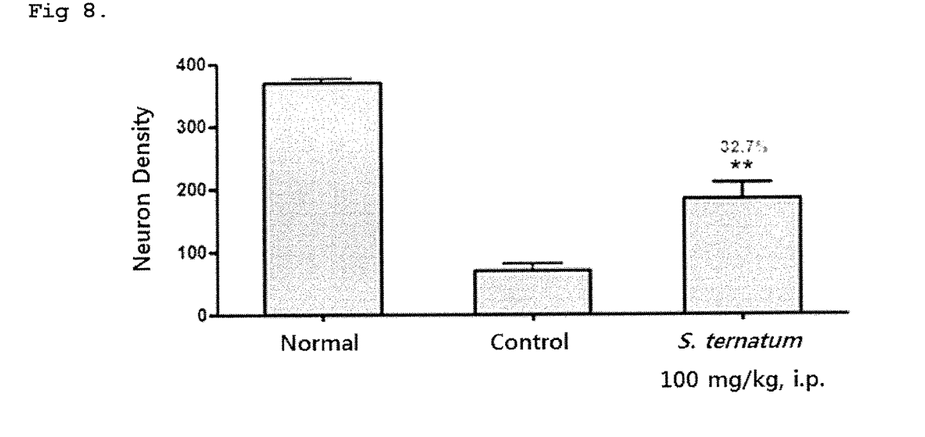
FIG. 8 is a graph of hippocampal cell densities compared between control and test groups in the 4-vessel occlusion (4-VO) models.

In addition, cells of the normal group numbered on average 379.4±14.6 within an area of width×length 1 mm², whereas 73.8±6.9 cells were counted on average in the control, indicating that the ischemia induced severe apoptosis. The test group administered with the *Sceptridium ternatum* extract at a dose of 100 mg/kg was found to have 173.8±64.8 cells/mm on average, which indicates an improvement in neuroprotective activity of 32.7% compared to the control (FIG. 8).

Formulation Example 1

Preparation of Powder

| | |
|---|---|
| The *S. ternatum* extract of Preparation Example | 300 mg |
| Lactose | 100 mg |
| Talc | 10 mg |

These ingredients were mixed and loaded into an airtight sac to produce a powder agent.

Formulation Example 2

Preparation of Tablet

| | |
|---|---|
| The *S. ternatum* extract of Preparation Example | 50 mg |
| Corn starch | 100 mg |
| Lactose | 100 mg |
| Magnesium stearate | 2 mg |

These ingredients were mixed and prepared into tablets using a typical tableting method.

Formulation Example 3

Preparation of Capsule

| | |
|---|---|
| The *S. ternatum* extract of Preparation Example | 50 mg |
| Corn starch | 100 mg |
| Lactose | 100 mg |
| Magnesium stearate | 2 mg |

These ingredients were mixed and loaded into gelatin capsules according to a typical method to produce capsules.

Formulation Example 4

Preparation of Injection

| | |
|---|---|
| The *S. ternatum* extract of Preparation Example | 50 mg |
| Sterile Distilled Water for injection | q.s. |
| pH modifier | q.s. |

These ingredients were employed in the above content per ampoule (23 ml) according to a typical method to produce injection.

Formulation Example 5

Preparation of Liquid

| | |
|---|---|
| The *S. ternatum* extract of Preparation Example | 1,000 mg |
| Sugar | 20 g |
| Fructose | 20 g |
| Lemon flavor | q.s. |

Pure water was added to form a total of 1,000 ml. Using a typical method, these ingredients were mixed, loaded into a brown bottle, and sterilized to give a liquid agent.

Formulation Example 6

Preparation of Health functional food

| | |
|---|---|
| The *S. ternatum* extract of Preparation Example | 1000 mg |
| vitamin mixture | q.s. |
| vitamin A acetate | 70 μg |
| vitamin E | 1.0 mg |
| vitamin B1 | 0.13 mg |
| vitamin B2 | 0.15 mg |
| vitamin B6 | 0.5 mg |
| vitamin B12 | 0.2 μg |
| vitamin C | 10 mg |
| biotin | 10 μg |
| nicotinic acid amide | 1.7 mg |
| folic acid | 50 μg |
| calcium pantothenate | 0.5 mg |
| mixture of minerals | q.s. |
| ferrous sulfate | 1.75 mg |
| zinc oxide | 0.82 mg |
| magnesium carbonate | 25.3 mg |
| potassium phosphate, monobasic | 15 mg |
| calcium phosphate, dibasic | 55 mg |
| potassium citrate | 90 mg |
| calcium carbonate | 100 mg |
| magnesium chloride | 24.8 mg |

Although the vitamins and minerals in the ratios are given as preferred relative amounts of ingredients suitable for health functional food, various modifications or changes in the mixing ratios are possible. The above ingredients may be mixed according to the conventional method of manufacturing health functional foods, and used for manufacturing health functional food compositions (e.g., nutrient candies) according to the conventional methods.

Formulation Example 7

Preparation of Health Functional Beverage

| | |
|---|---|
| The *S. ternatum* extract of Preparation Example | 1000 mg |
| Citric acid | 1000 mg |
| Oligosaccharide | 100 g |
| Japanese apricot concentrate | 2 g |
| Taurine | 1 g |
| Pure water | added to form a total volume of 900 ml |

According to a typical manufacturing method, these ingredients were admixed, and heated for 1 hrs at 85° C. while stirring. The solution thus obtained was filtered and placed in a sterile 2 L container which was sealed and sterilized. The resulting solution was stored in a refrigerator until use in preparing health functional beverages.

Although the ingredients in the ratio are given as preferred embodiments suitable for favorite beverages, various modifications or changes in the mixing ratios are possible according to regional and national preferences, such as target consumer, country, purpose, etc.

INDUSTRIAL APPLICABILITY

In accordance with the present invention, a composition is provided for preventing or treating strokes or degenerative brain diseases.

The invention claimed is:

1. A method of treating a cerebral ischemia-induced degenerative brain disease, comprising administering to a subject in need thereof an effective amount of a composition comprising a *Sceptridium ternatum* extract as an active ingredient.

2. The method of claim 1, wherein the degenerative brain disease is dementia.

3. The method of claim 1, wherein the *Sceptridium ternatum* extract is obtained from a whole *Sceptridium ternatum* plant.

4. The method of claim 1, wherein the *Sceptridium ternatum* extract is obtained with an extraction solvent selected from the group consisting of water, an alcohol, and a mixture thereof.

* * * * *